US009056702B2

(12) United States Patent
Hatalla

(10) Patent No.: US 9,056,702 B2
(45) Date of Patent: Jun. 16, 2015

(54) CLOSURE FOR CONTAINERS

(75) Inventor: Chris Daniel Hatalla, Woodbury, MN (US)

(73) Assignee: Nestec S.A., Vevey (CH)

( * ) Notice: Subject to any disclaimer, the term of this patent is extended or adjusted under 35 U.S.C. 154(b) by 1088 days.

(21) Appl. No.: 13/063,144

(22) PCT Filed: Sep. 1, 2009

(86) PCT No.: PCT/US2009/055573
§ 371 (c)(1),
(2), (4) Date: Jan. 25, 2012

(87) PCT Pub. No.: WO2010/030528
PCT Pub. Date: Mar. 18, 2010

(65) Prior Publication Data

US 2012/0136333 A1 May 31, 2012

Related U.S. Application Data

(60) Provisional application No. 61/096,426, filed on Sep. 12, 2008.

(51) Int. Cl.

| | |
|---|---|
| ***A61B 19/00*** | (2006.01) |
| ***B65D 51/00*** | (2006.01) |
| ***B65D 51/16*** | (2006.01) |
| *A61J 1/14* | (2006.01) |

(52) U.S. Cl.
CPC ......... *B65D 51/002* (2013.01); *Y10T 29/49833* (2015.01); *A61J 1/14* (2013.01); *B65D 51/1616* (2013.01)

(58) Field of Classification Search
CPC ............ A61J 1/14; A61J 1/05; A61J 1/1406; A61J 1/1412; A61J 1/1475; A61J 2001/1443; A61J 2001/145; B65D 51/18; B65D 51/20; B65D 25/107; B65D 47/06; B65D 47/12
See application file for complete search history.

(56) References Cited

U.S. PATENT DOCUMENTS

| | | | | |
|---|---|---|---|---|
| 5,782,383 | A | 7/1998 | Robinson | |
| 6,709,424 | B1 * | 3/2004 | Knierbein | 604/411 |
| 6,959,615 | B2 * | 11/2005 | Gamble | 73/863.71 |
| 7,452,348 | B2 | 11/2008 | Hasegawa | |

(Continued)

FOREIGN PATENT DOCUMENTS

| | | |
|---|---|---|
| AU | 2009291983 | 3/2010 |
| EP | 0298247 | 1/1989 |
| EP | 0485342 | 5/1992 |

(Continued)

*Primary Examiner* — Leslie Deak
*Assistant Examiner* — Kai Weng
(74) *Attorney, Agent, or Firm* — K&L Gates LLP

(57) ABSTRACT

Closures for containers and methods for using same are provided. In a general embodiment, the present disclosure provides a closure having a top portion (12), a bottom portion (14) and a side portion (16), an aperture (18) extending though the closure, a projection (20) extending from the closure and at least two rib members (36) on an interior of the projection. The projection may also include a cover. In another embodiment, a method for using a closure includes inserting a spike member into a projection, piercing a membrane (28) that hermetically seals a medical container, pushing rib members within the projection to center the spike member inserted into the projection, and tearing the membrane to create a vent hole in the membrane.

25 Claims, 4 Drawing Sheets

(56) References Cited

U.S. PATENT DOCUMENTS

| | | | | |
|---|---|---|---|---|
| 2008/0015539 | A1* | 1/2008 | Pieroni et al. | 604/403 |
| 2008/0197100 | A1* | 8/2008 | Faulconnier et al. | 215/250 |

FOREIGN PATENT DOCUMENTS

| | | |
|---|---|---|
| EP | 1035029 | 9/2000 |
| JP | 06-086812 | 3/1994 |
| JP | 06086812 | 3/1994 |
| JP | 08-299417 | 11/1996 |
| JP | 08299417 | 11/1996 |
| JP | 2002506685 | 3/2002 |
| JP | 2004-194953 | 7/2004 |
| JP | 2004194953 | 7/2004 |
| JP | 2010/030528 | 3/2010 |
| WO | 99/47098 | 9/1999 |

* cited by examiner

CLOSURE FOR CONTAINERS

CROSS REFERENCE TO RELATED APPLICATIONS

The present application is a National Stage of International Application No. PCT/US09/55573, filed on Sep. 1, 2009, which claims priority to U.S. Provisional Application No. 61/096,426, filed on Sep. 12, 2008, the entire contents of which are being incorporated herein by reference.

BACKGROUND

The present disclosure relates generally to closures for containers. More specifically, the present disclosure relates to closures for containers that allow for easy and accurate delivery of a nutritional or medical fluid from a container.

Closures for containers that are used for storing nutritional or medical fluids are known in the art. An example of this type of container is a hermetically sealed container having a penetrable membrane cover that prevents contamination of the fluid before use. It is common for closures of such containers to have openings, or ports, wherein devices for puncturing the membrane of the container may be inserted to access the fluid. However, these types of closures do not always ensure that the punctured membrane will provide proper ventilation to the container during withdrawal of fluids therefrom. Consequently, containers having these types of closures may be susceptible to collapsing upon themselves during withdrawal of the fluids.

SUMMARY

The present disclosure relates generally to the packaging and delivery of a fluid from a container. More specifically, the present disclosure relates to closures for medical containers and methods of using same. The closures of the present disclosure may be used, for example, for allowing easy delivery of a medical fluid in a fluid receptacle to a patient.

Pursuant to an embodiment of the present disclosure, a closure for a container is provided. The closure includes a projection extending from a top portion of the closure. The projection has at least two rib members located on an interior of the projection. The projection is designed to receive a spike or other fluid connection member. The projection is also designed to be incompatible with intravenous spike sets. The incompatibility is caused, at least in part, by the inner diameter of the projection being larger than an outer diameter of a shoulder of an intravenous spike. In an embodiment, the projection and the spike member are threaded.

In an embodiment, the closure includes a bottom portion and a side portion. The top and bottom portions may be substantially planar and the side portion may be substantially cylindrical. The side portion may include at least one raised member.

In an embodiment, the bottom portion includes a filter. The filter may be secured to the bottom portion by heat staking. The bottom portion may also include a liner.

In an embodiment, the closure includes at least one aperture extending from the top portion through the bottom portion.

In an embodiment, the projection includes a cover.

In an embodiment, the closure is formed from a thermoplastic polymer material selected from the group consisting of polypropylene, polyethylene or combinations thereof. In an embodiment, the closure is formed from polypropylene.

In an embodiment, the projection is substantially cylindrical.

In an embodiment, the rib members are located about 180° from each other on an interior portion of the projection.

In an embodiment, the projection includes three rib members. In this embodiment, the rib members may be located about 120° from each other on an interior portion of the projection.

In an embodiment, the rib members have a shape selected from the group consisting of polygonal, semi-circular, oblong or combinations thereof. In an embodiment, the rib members have a polygonal shape selected from the group consisting of rectangular, square, triangular, trapezoidal or combinations thereof.

In an embodiment, a bottom portion of the rib members extend at an angle of about 45° to a vertical axis extending through a center of the projection.

In an embodiment, the rib members are formed from a thermoplastic polymer material selected from the group consisting of polypropylene, polyethylene or combinations thereof.

In another embodiment, a container is provided. The container includes a receptacle and a closure. The receptacle defines and interior and houses a liquid. The closure is configured for connection to the receptacle, and includes a projection having at least two rib members located on an interior of the projection. The projection is designed to receive a spike or other connection member to access the fluid in the container. The projection is also designed to be incompatible with intravenous spike sets. The incompatibility is caused, at least in part, by the inner diameter of the projection being larger than an outer diameter of a shoulder of an intravenous spike.

In an embodiment, the receptacle includes a membrane sealed to at least a portion of the receptacle.

In an embodiment, as noted above, the container can receive a fluid delivery device so configured and arranged to be connected to the closure. The fluid delivery device may include a spike member. The fluid delivery device may also include a medical tube selected from the group consisting of gastrostomy, percutaneous, jejunostomy, nasogastric or combinations thereof.

In yet another embodiment, a method for connecting a fluid delivery device to a fluid receptacle is provided. The method includes inserting a spike member of the fluid delivery device into a projection in a first direction. The projection is located on a closure attached to the fluid receptacle. The method further includes contacting at least two rib members located on an interior of the projection with the spike member, piercing a membrane of the fluid receptacle with the spike member and securing the spike member onto the projection.

In an embodiment, the spike member is secured onto the projection using a technique selected from the group consisting of press-fitting, snap-fitting, threading, friction-fitting or combinations thereof.

In an embodiment, the spike member includes a sheath having internal threads. In an embodiment, the projection includes external threads. A fluid-tight seal is formed between the sheath and the projection when the sheath is threaded onto the projection.

In an embodiment, the method includes bending the at least two rib members in a second direction during threading. The second direction being different from the first direction.

In an embodiment, the projection is so constructed and arranged so as to be incompatible with intravenous spike sets. In this way, the projection may have an inner diameter that is larger than an outer diameter of a shoulder of an intravenous spike.

In still yet another embodiment, a method for delivering a medical fluid to a patient is provided. The method includes inserting a spike member into a projection in a first direction, wherein the projection is located on a closure. The method further includes piercing a membrane of a fluid receptacle with the spike member, pushing at least two rib members located on an interior of the projection in a second direction different from the first direction, tearing the membrane with the spike member and delivering the medical fluid to a patient.

In an embodiment, the method includes forming a ventilation hole during tearing of the membrane.

In an embodiment, the medical fluid is delivered through the spike member.

In an embodiment, the closure includes an aperture that extends through a top surface and a bottom surface of the closure.

In an embodiment, the method includes threading the spike member onto the projection. A fluid-tight seal is formed between the spike member and the projection when the spike member is threaded onto the projection.

In an embodiment, the method includes attaching the spike member to a medical tube selected from the group consisting of gastrostomy, percutaneous, jejunostomy, nasogastric or combinations thereof.

In an embodiment, the projection is so constructed and arranged so as to be incompatible with intravenous spike sets. In this way, the projection may have an inner diameter that is larger than an outer diameter of a shoulder of an intravenous spike.

An advantage of the present disclosure is to provide improved closures for containers.

Another advantage of the present disclosure is to provide improved closures for delivery of nutritional or medical fluids from medical containers.

Still yet another advantage is to decrease the number of human errors associated with tube-feed connections.

A further advantage of the present disclosure is to provide a more secure fit between containers, and specifically closures, and fluid delivery devices such as spikes.

An advantage of the present disclosure is to reduce the risk of contamination and formula waste for medical formulations.

Yet another advantage of the present disclosure is to prevent the collapse of medical bottles during delivery of the medical fluid.

Additional features and advantages are described herein, and will be apparent from the following Detailed Description and the figures.

DETAILED DESCRIPTION

The present disclosure is generally directed to closures for containers. More specifically, the present disclosure is directed to closures for containers that may be used to house for nutritional or medical fluids. The closure is designed to provide access to the fluid contained within the container. For example, the closures of the present disclosure include rib members that are designed to guide a spike member into a projection that extends from a top portion of the closure in such a manner that the spike member will self-center within the projection. As the spike member self-centers, the spike member tears a penetrable membrane of the container to create a ventilation hole, which prevents the container from collapsing upon itself during delivery of the fluid from the container. Specifically, the ventilation hole allows for the introduction of clean air into the container as the fluid within the container is being withdrawn through the spike member. Moreover, the present disclosure is also directed toward methods for using such closures.

Figure 1:
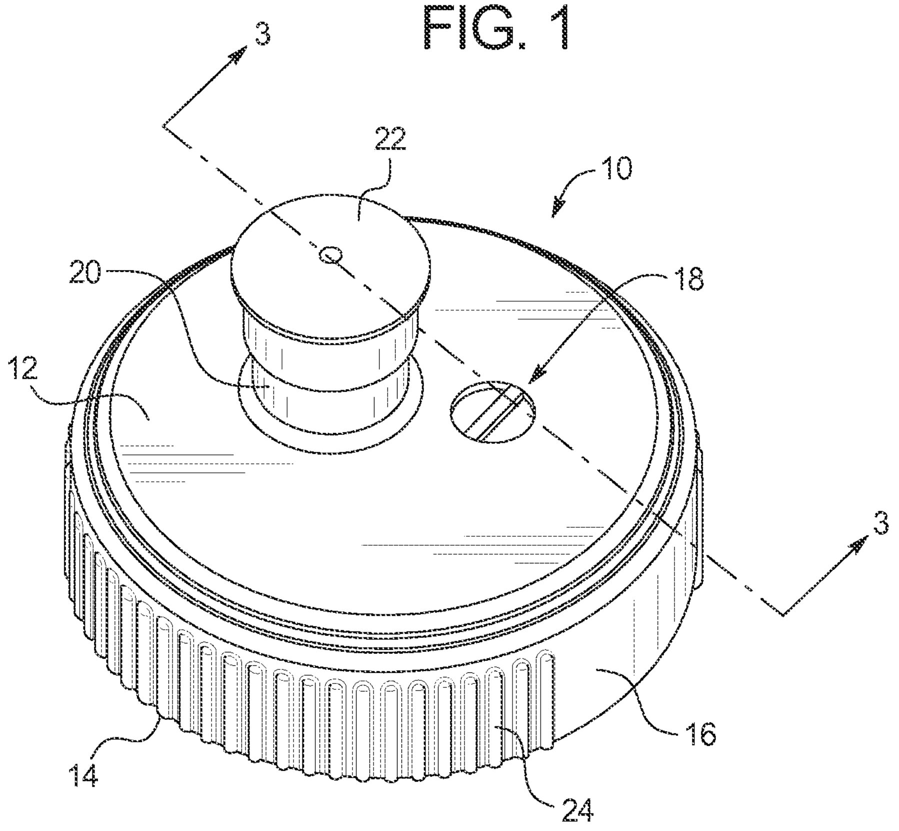
FIG. 1 illustrates a perspective view of a closure for a container in accordance with an embodiment of the present disclosure.

As is shown in FIG. 1, an embodiment of a closure of the present disclosure is generally designated by the numeral 10. The closure 10 includes a top portion 12, a bottom portion 14, a side portion 16, an aperture 18, a projection 20 and a cap 22. In an embodiment, the closure 10 also includes raised members 24 on the side portion 16, which may allow for easy attachment of the closure 10 to a container. Specifically, the raised members 24 may help ensure that a user of the closure 10 has a sufficient grip on the closure 10 to securely attach the closure 10 to a container or has a sufficient grip on the closure 10 and container during use of same. However, in an embodiment, the closure 10 may be ultra-sonically welded to a container so that it cannot be unscrewed on by a user. Although the closure 10 is shown in the present Figures as including raised members 24, the skilled artisan will appreciate that the closure 10 need not necessarily include the raised members 24.

Figure 2:
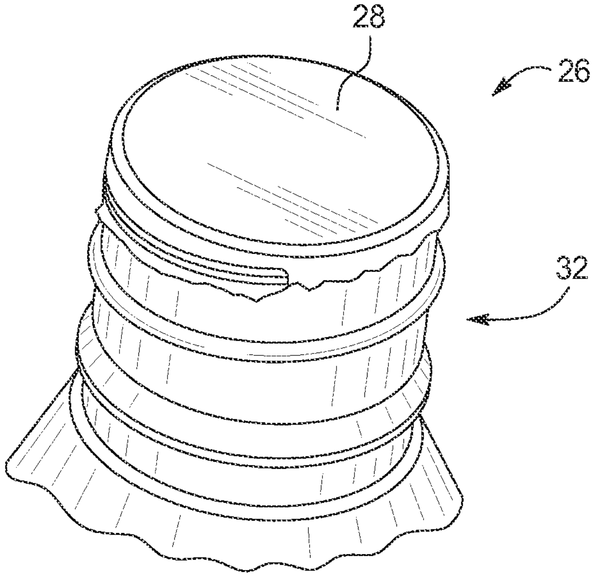
FIG. 2 illustrates a perspective view of a container in accordance with an embodiment of the present disclosure.

FIG. 2 illustrates a container 26 that may be used in combination with a closure 10 of the present disclosure. In an embodiment, the container 26 may be a medical container that is a fluid receptacle for nutritional or medical fluid and, as such, the container 26 must be capable of preventing the fluids from becoming contaminated during shipping or storage of the container 26. Therefore, the container 26 is generally provided with a penetrable membrane 28 that hermetically seals the container 26 from the surrounding environment and prevents the ingress of air and/or bacteria from the environment, which are common sources for the contamination of nutritional and medical fluids within such containers 26.

Figure 3:
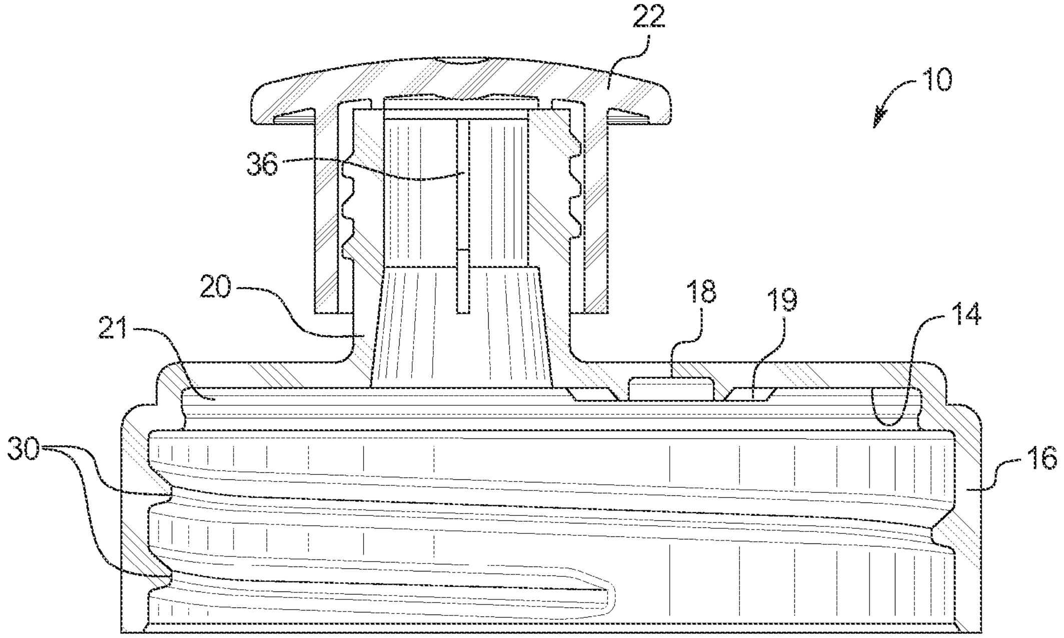
FIG. 3 illustrates a cross-sectional view of a closure for a container in accordance with an embodiment of the present disclosure and taken along line 3-3 of FIG. 1.

In addition to the penetrable membrane 28, the container 26 also includes a threaded neck portion 32 that allows the closure 10 of the present disclosure to connect thereto. For example, in an embodiment, the closure 10 includes threads 30 on an interior of the side portion 16, as is shown in FIG. 3. The threads 30 may be used to connect the closure 10 to the container 26 by engaging the threaded neck portion 32 of the container 26. In other words, the threads 30 are used to screw the closure 10 onto the container 26. In an embodiment, the closure 10 may be ultra-sonically welded to the container 26 after is it threaded onto the container 26. The skilled artisan will immediately appreciate, however, that the closure 10 need not necessarily include threads 30 to connect the closure 10 to the container 26. Instead, the closure 10 may include other physical characteristics that may be used to connect to the container 26. For example, the closure 10 may include recessed ring(s) (not shown) along an interior of the side portion 16 that may be used to snap-fit the closure 10 around corresponding raised ring(s) of a neck portion of the container 26. In another embodiment, the closure 10 may also be spin-welded to the container 26.

In an embodiment, and as is also shown in FIG. 3, the closure 10 includes a filter 19 and a liner 21. The filter 19 will be secured to the bottom portion 14 of the closure 10 at a location that corresponds to the location of the aperture 18. The filter 19 is designed as a hydrophobic/oleophobic air-borne bacteria filter and will, therefore block the flow of a water- or oil-based liquid from exiting the closure. The filter 19 may be fabricated from a woven, synthetic, semi-permeable fiber material. In use, as will be described in greater detail below, the filter 19 is designed so that it will be in contact the fluid of the container 26. Consequently, the filter 19 will become wet and will permit the introduction of atmospheric air from the aperture 18 to pass through the filter 19 and into the container 26 through a ventilation hole, the formation of which will also be discussed below. The primary function of the filter 19, however, is to allow the atmospheric air to pass into the container 26 while, at the same time, filtering out the bacteria and germs from the air. The filter 19 may be secured to the bottom portion 14 of the closure 10 by any methods known in the art. In an embodiment, however, the filter 19 is secured to the bottom portion 14 of the closure 10 by heat staking, which occurs when two materials are brought together in the presence of sufficient heat and pressure so as to form one material.

The closure 10 of the present disclosure may also include a liner 21 that functions as a gasket, which forms a mechanical seal that fills the space between the bottom portion 14 of the closure 10 and a neck portion of a corresponding container 26. The liner 21 may be manufactured by cutting from sheet materials including, but not limited to, gasket paper, rubber, silicone, metal, cork, felt, a synthetic rubber such as Neoprene®, nitrile rubber, fiberglass, or a plastic polymer such as polychlorotrifluoroethylene. The liner 21 is generally shaped to fit a portion of the bottom portion 14 of the closure 10 and generally has a central aperture of approximately the same size or slightly smaller than the size of a neck portion of a container 26. The liner 21 should be formed from a material that is to some degree compressible so that it tightly fills the space it is designed for, including any slight irregularities. In an embodiment, the liner 21 is a foam liner.

Similar to the filter 19, the liner 21 of the closure 10 also contacts the bottom portion 14 of the closure 10 and may also be secured to the bottom portion 14 by any methods known in the art. In an embodiment, the liner 21 is secured to the bottom portion 14 of the closure 10 by snap-fitting the liner 21 into the bottom portion 14 of the closure 10. Although it may not be necessary for the liner 21 to be secured to the bottom portion 14 of the closure 10, the liner 21 must form a fluid tight seal between the bottom portion 14 of the closure 10 and the neck portion of a corresponding container 26. Similarly, although the Figures illustrate the closure 10 as having a liner 21, the skilled artisan will appreciate that the closure 10 need not necessarily have a liner 21 and may be designed such that it still creates a fluid tight seal with a container 26.

Although many of the present Figures illustrate the closure 10, generally, and the side portion 16, specifically, as having a cylindrical shape, the skilled artisan will appreciate that the closure 10 and/or side portion 16 may have any shape known in the art for container closures. For example, the closure 10 may be substantially square-shaped and have a substantially cylindrically-shaped interior that may be connected to a substantially cylindrically-shaped container neck portion. Similarly, the closure 10 may be substantially square-shaped and have a substantially square-shaped interior that may be snap-fit to a substantially square-shaped container neck portion.

In an embodiment, the top and bottom portions 12, 14, respectively, of the closure 10 may be planar surfaces. Accordingly, to retain the shape of the closure 10, the closure 10 may be formed from any semi-rigid material that is capable of maintaining a pre-determined shape. For example, the closure 10 may be formed from a thermoplastic polymer material selected from the group consisting of polypropylene, polyethylene or combinations thereof. In an embodiment, the closure 10 is formed from polypropylene. However, the skilled artisan will appreciate that the top and bottom portions 12, 14 need not be planar surfaces and may also have any shape known in the art for container closures. Accordingly, it will also be appreciated that the closure 10 need not be formed from a thermoplastic polymer material and may be formed from any material known in the art for container closures. It will be understood that the closure 10 of the present disclosure will not be limited by any of the illustrated physical characteristics of the closure 10 including, but not limited to, the shape of the closure 10, the material from which the closure 10 is formed and the method of connecting the closure 10 to the container 26.

During shipping and storage of the container 26, the closure 10 is connected to the container 26, as discussed above. In addition to the penetrable membrane 28 of the container 26, the closure 10 also includes a cap 22 that fits onto the projection 20 and that reduces the likelihood of contamination between the container 26 and the closure 10. In this way, the cap 22 will prevent any bacteria or germs from entering the projection 20 of the closure 10, thereby preventing the transfer of the bacteria or germs from the closure 10 to a patient through medical devices that are inserted into the projection 20 such as, but not limited to, a medical device having a spike member, or a cannula.

As discussed previously with respect to the closure 10, the cap 22 may also be formed from any material known in the art and used for container closures. In an embodiment, the cap 22 is formed from a thermoplastic polymer material selected from the group consisting of polypropylene, polyethylene or combinations thereof. In an embodiment, the cap 22 is formed from polypropylene.

The cap 22 may be connected to the projection 20 through techniques that are similar to those discussed above with respect to the connection of the closure 10 to the container 26. For example, the cap 22 may include interior threads (not shown) that are used to screw the cap 22 onto the exterior threads 34 of the projection 20. The cap 22 may also include recessed ring(s) (not shown) along an interior that may be used to snap-fit the cap 22 around corresponding raised ring(s) of the projection 20. In an embodiment, the cap 22 includes a plurality of chevron-shaped projections (not shown) that extend outward from an interior side portion of the cap 22 and that are designed to interact with the external threads 34 of the projection 20 to ensure that the cap 22 remains in place during shipping and storage of the closure 10 and container 26. Immediately before use of the nutritional or medical fluids, the consumer is able to pull the cap 22 off of the projection 20, thereby exposing the interior of the projection 20 to the environment.

Figure 4:
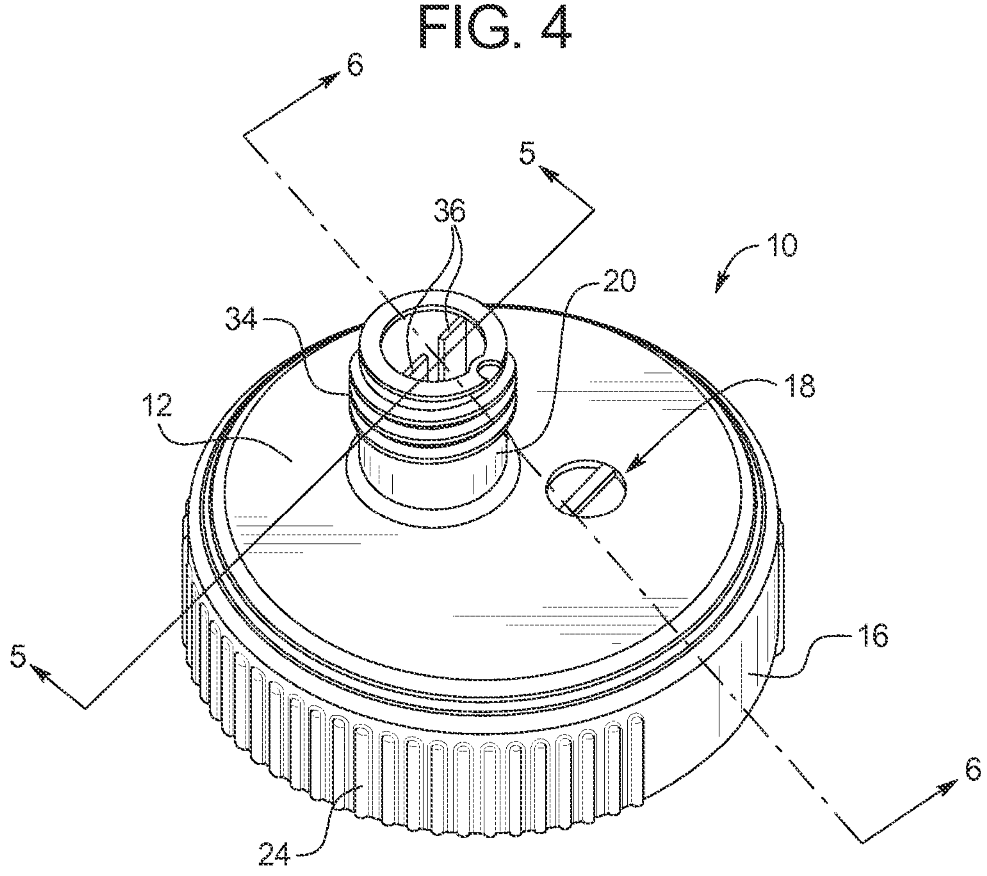
FIG. 4 illustrates a perspective view of a closure in accordance with an embodiment of the present disclosure.
Figure 5:
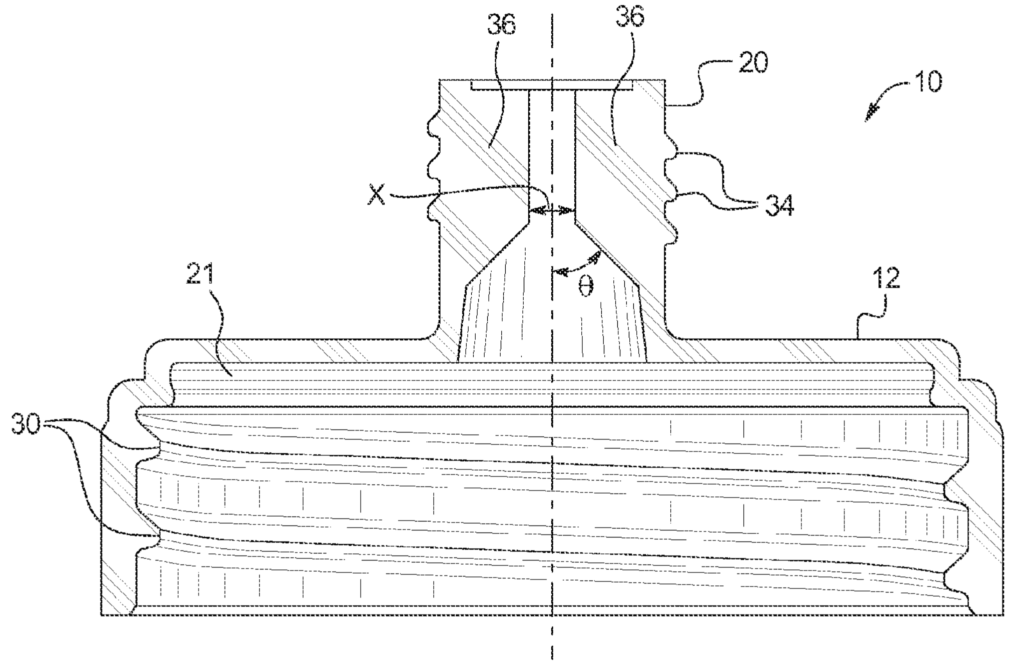
FIG. 5 illustrates a cross-sectional view of a closure for a container in accordance with an embodiment of the present disclosure and taken along line 5-5 of FIG. 4.

FIG. 4-5 illustrate the closure 10 after the cap 22 has been removed. As can be seen from FIGS. 3-5, the interior of the projection 20 includes at least two rib members 36 that extend inward toward the center of the projection 20 and act, at least in part, as guide members for the insertion of a spike member 38 into the projection 20, which is used to access the fluid within the container 26. The projection 20 and the rib members 36 are associated with the cannulation of the closure 10, as will be discussed further below. Generally, the rib members 36 aid in forming a ventilation hole in a membrane 28 of a container 26, which allows for the introduction of clean air into the container 26 during withdrawal of a fluid from the container 26 through the spike Member 38. This ventilation hole helps to prevent the container 26 from forming a vacuum and collapsing on itself during withdrawal.

As illustrated, the rib members 36 may be located exactly opposite each other on an interior of the projection 20. In an embodiment, the rib members 36 are located on the interior of a substantially cylindrical projection 20 and, therefore, are located about 180° from each other. Although the Figures show that the projection 20 includes two rib members 36, the skilled artisan will appreciate that the projection 20 may include more than two rib members 36. For example, in an embodiment, the projection 20 includes three rib members 36, which are located about 120° from each other along the interior of a substantially cylindrical projection 20. Similarly, the skilled artisan will also appreciate that the rib members 36 need not be spaced equidistant along the interior of the projection 20 and may have any spacing that allows the rib members 36 to properly guide the spike member 38 into position within the projection 20.

The rib members 36 of the projection 20 may have any shape necessary to properly guide a spike member 38 into proper alignment within the projection 20. For example, the rib members 36 may have a shape selected from the group consisting of polygonal, semi-circular, oblong or combinations thereof. The rib members 36 may also have a polygonal shape selected from the group consisting of rectangular, square, triangular, trapezoidal or combinations thereof.

In an embodiment, the rib members 36 have a substantially trapezoidal shape, as is shown by FIG. 5. In other words, in this embodiment, the rib members 36 are shaped substantially as quadrilaterals (a closed plane shape with four linear sides) that have at least one pair of parallel lines for sides. Of the two remaining non-parallel sides, one of the sides (e.g., a bottom side of the rib member 36) is angled such that the side forms an angle of about 20° to about 70° with a vertical axis that extends through the center of the projection 20 as is illustrated by the angle θ in FIG. 5. In an embodiment, the side is angled such that the side forms an angle of about 30° to about 60° with a vertical axis that extends through the center of the projection 20. In another embodiment, the angle is about 45°. It is believed that a 45° angle provides advantages that allow for easy insertion and alignment of spike members 38 into the projection 20. However, the skilled artisan will immediately appreciate that the rib members 36 are not limited to the shapes or angles disclosed herein and may encompass any shape or angle that may be useful for inserting and guiding spike members 38.

Just as the rib members 36 can have different shapes, the rib members 36 may also have different sizes. For example, the rib members 36 may extend into the interior of the projection 20 only slightly such that there is a large gap (the gap being identified, for example, as the variable "x" in FIG. 5) between the two rib members 36. In contrast, the rib members 36 may extend a greater distance into the interior of the projection 20 such that the gap, x, between the rib members 36 is minimal. The skilled artisan will appreciate that the flexibility or rigidity and, as such, the materials from which the rib members 36 are formed may impact the size of the rib members 36. In an embodiment, the rib members 36 are formed from a thermoplastic polymer material selected from the group consisting of polypropylene, polyethylene or combinations thereof. In an embodiment, the rib members 36 are formed from polypropylene.

Figure 6:
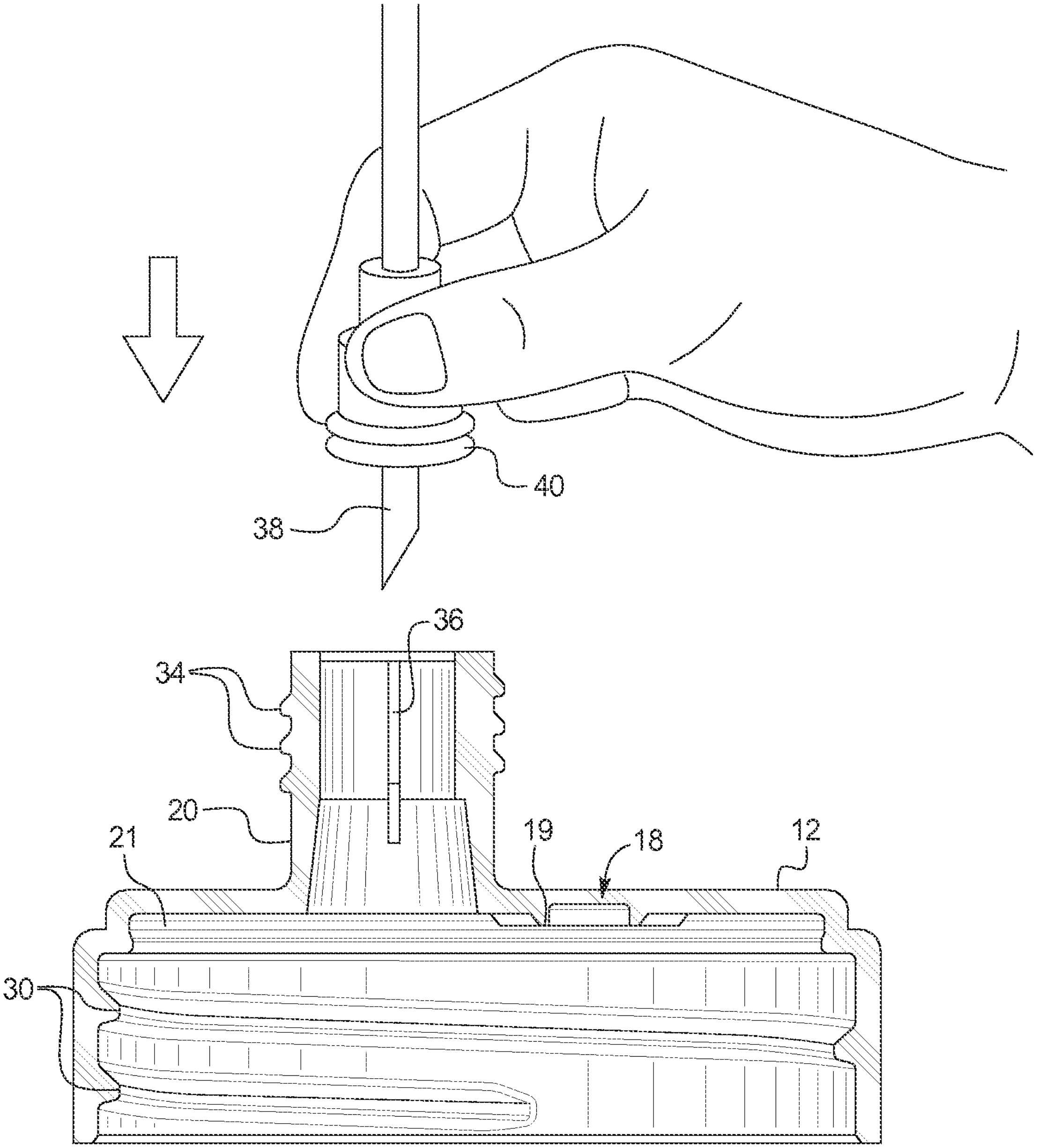
FIG. 6 illustrates a cross-section view of a closure for a container in accordance with an embodiment of the present disclosure and taken along line 6-6 of FIG. 4.

As is shown by FIG. 6, after the cap 22 is removed from the projection 20, the contents of the container 26 may be accessed by inserting a spike member 38 into the projection 20. In an embodiment, the spike member 38 is a cannula, which can be inserted into the body for the delivery or removal of fluid. The spike member 38 may be a part of a fluid delivery device including a medical tube selected from the group consisting of gastrostomy, percutaneous, jejunostomy, nasogastric or combinations thereof. In an embodiment, the spike member 38 is adhesively bonded to a medical tube.

Generally speaking, however, the closure 10 of the present disclosure is so constructed and arranged such that the closure 10 is incompatible with fluid delivery devices such as intravenous spike sets that include intravenous spikes. In this manner, the projection 20 may be designed to have an inner diameter that is larger than an outer diameter of a typical intravenous spike or cannula. The intravenous spike set may be any known intravenous spike set. As such, attempts to connect the projection 20 of the present closure 10 with an intravenous spike set may result in leakage of the fluid from within the container 26 or an improper connection that results in the intravenous spike set falling out of the projection 20. The incompatibility between the projection 20 of the present closure 10 with an intravenous spike set, therefore, may decrease the number of tubing misconnections that result from human error wherein fluids such as, for example, enteral fluids are improperly fed directly into the venous system. Instead, the closure 10 of the present disclosure will ensure that the fluids within the container 26 will be fed into the body through the proper channels.

The spike member 38 and the projection 20 may be connected by threading a sheath 40 of the spike member 38, which has internal threads (not shown), onto the external threads 34 of the projection 20. The insertion of the spike member 38 is usually performed while the container 26 and closure 10 are in an upright position. Once the sheath 40 has been completely threaded onto the projection 20, there exists a fluid-tight seal between the sheath 40 and the projection 20. As discussed above, however, the connection between the spike member 38 and the projection 20 need not be connected by threading and may be connected by other techniques including, but not limited to, press-fitting, snap-fitting, friction-fitting and adhesives. After the establishment of the fluid-tight seal between the sheath 40 and the projection 20, the closure 10 and container 26 may be inverted to withdraw the fluid from the container 26.

As the spike member 38 is inserted into the projection 20, the tip of the spike member 38 will contact a top portion of the rib members 36 and will be guided by the rib members 36 to one side of both of the rib members 36. In other words, the spike member 38 may contact a top portion of the rib members 36 as it is inserted into the projection 20 and, because the rib members 36 are formed of a sufficiently rigid, yet flexible material, the rib members 36 do not immediately give to the movement of the spike member 38. Instead, the rib members 36 remain in position and force the spike member 38 to be inserted either to the right or to the left of both of the rib members 36. For example, if the spike member 38 contacts a top portion of the rib members 36 and is guided to the left of the rib members 36, the spike member 38 will be inserted into the projection 20 to the left of the rib members 36 and will contact the left side of the internal portion of the projection 20. Similarly, if the spike member 38 contacts a top portion of the rib members 36 and is guided to the right of the rib members 36, the spike member 38 will contact the right side of the internal portion of the projection 20.

As the spike member 38 is pushed further down into the projection 20, the tip of the spike member 36 will reach the bottom portion 14 of the closure 10, which is immediately adjacent the penetrable membrane 28 of the container 26 when the closure 10 is connected to the container 26. As the spike member 38 is pushed past the bottom portion 14 of the closure 10, the spike member 38 contacts the penetrable membrane 28 and punctures the membrane 28. Because the spike member 38 has been guided to the right or to the left of the rib members 36, the initial puncture will occur at either the right or left side of the projection 20. As the sheath 40 begins to thread onto the projection 20, the spike member 38 begins to self-center within the projection 20 and begins to push the rib members 36 in a direction that is substantially perpendicular to the direction of the insertion of the spike member 38. As the rib members 36 are pushed, the rib members 36 bend sufficiently to allow the spike member 38 to self-center within the projection 20.

For example, if the spike member 38 is guided by the rib members 36 to the left of the rib members 36 upon the initial insertion of the spike member 38, as the spike member 38 begins to self-center within the projection 20 during threading of the sheath 40 onto the projection 20, the spike member 38 will push the rib members 36 to the right so that the rib members 36 will bend and allow the spike member 38 to occupy the space in the center of the projection 20 once occupied by the rib members 36. The rib members 36 will now be bent to the right such that the rib members 36 no longer extend directly toward each other.

During self-centering of the spike member 38 and bending of the rib members 36, the spike member 38 tears the penetrable membrane 28 of the container 26 as the spike member 38 self-centers. This tear (not shown) is a result of the movement of the spike member 38 after the initial penetration of the membrane 28. For example, if the spike member 38 is initially guided by the rib members 36 to insert into the projection 20 to the left of the rib members 36, then the spike member 38 will initially puncture a portion of the membrane 28 that is located on the left half of an area of the membrane 28 corresponding to the shape of the projection 20 and located directly below the projection 20. As the spike member 38 self-centers during threading of the sheath 40 onto the projection 20, the spike member 38 will tear the membrane 28 from the initial puncture, which is on the left half of an area of the membrane 28 corresponding to the shape of the projection 20, to the right of the initial puncture until the spike member 38 is centered.

As a result of the tearing of the membrane 28 during threading, the membrane 28 will have a ventilation hole (not shown) where the initial puncture of the spike member 38 occurred since the spike member 38 no longer occupies the space. This ventilation hole works in conjunction with the aperture 18 and filter 19 to allow atmospheric air to enter into the container 26 during delivery of the fluid within the container 26. For example, in the inverted position, the fluid passes from the container 26 through the ventilation hole in the membrane 28 where the fluid wets the filter 19. As long as the filter 19 remains wet, it permits introduction of the atmospheric air into the container 26 in a pathway that is opposite that of the fluid. In other words, the atmospheric air enters the aperture 18, travels through the wetted filter 19 and is then able to enter into the container 26 through the ventilation hole. By providing a source of clean air to the container 26 as liquid is being withdrawn from the container 26, the container 26 does not create a vacuum and collapse upon itself.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:

1. A closure for a container, the closure comprising:

a projection extending from a top portion of a base of the closure, the projection defining an interior having a substantially tubular shape and comprising at least two rib members located on the interior; wherein: a) the base comprising a bottom portion and a side portion; b) the top and bottom portions are substantially planar; c) the side portion is substantially cylindrical; and d) wherein the projection is so constructed and arranged so as to be incompatible with an intravenous spike set, wherein the at least two rib members are constructed and arranged to be bent in a direction that is substantially perpendicular to a direction of insertion of a spike member into the closure, wherein the at least two rib members each comprise a face extending substantially parallel to a vertical axis through a center of the projection, the face being exposed for contacting the spike member.

2. The closure of claim 1, the bottom portion comprising a filter.

3. The closure of claim 2, wherein the filter is secured to the bottom portion by heat staking.

4. The closure of claim 1, the bottom portion comprising a liner.

5. The closure of claim 1, the side portion comprising at least one raised member.

6. The closure of claim 1, the closure comprising at least one aperture extending from the top portion through the bottom portion.

7. The closure of claim 1, the projection comprising a cover.

8. The closure of claim 1, wherein the closure is formed from a thermoplastic polymer material selected from the group consisting of polypropylene, polyethylene and combinations thereof.

9. The closure of claim 1, wherein the closure is formed from polypropylene.

10. The closure of claim 1, wherein the projection is substantially cylindrical.

11. The closure of claim 10, the projection comprising three rib members.

12. The closure of claim 1, the rib members comprising a shape selected from the group consisting of polygonal, semicircular, oblong and combinations thereof.

13. The closure of claim 1, wherein a bottom portion of the rib members extend at an angle of about 45° to a vertical axis extending through a center of the projection.

14. A container for housing a fluid, the container comprising: a receptacle defining an interior for receiving the fluid; and the closure of claim 1.

15. The container of claim 14, the receptacle comprising a membrane sealed to at least a portion of the receptacle.

16. The container of claim 14, the container comprising a fluid delivery device so constructed and arranged to be connected to the closure.

17. The container of claim 16, the fluid delivery device comprising the spike member.

18. A method for connecting a fluid delivery device to a fluid receptacle, the method comprising:

inserting a spike member of the fluid delivery device into a projection in a first direction, wherein the projection is located on a closure attached to the fluid receptacle and wherein the spike member is secured onto the projection using a technique selected from the group consisting of snap-fitting, press-fitting, threading, friction-fitting and combinations thereof;

contacting at least two rib members located on an interior of the projection with the spike member;

piercing a membrane of the fluid receptacle with the spike member; and securing the spike member onto the projection, wherein the projection is so constructed and arranged so as to be incompatible with an intravenous spike set, wherein the at least two rib members are constructed and arranged to be bent in a direction that is substantially perpendicular to a direction of insertion of the spike member into the closure, wherein the at least two rib members each comprise a face extending substantially parallel to a vertical axis through a center of the projection, the face being exposed for contacting the spike member.

19. The method of claim 18, the spike member comprising a sheath comprising internal threads and the projection comprising external threads.

20. A method for delivering a medical fluid to a patient, the method comprising:

inserting a spike member into a projection in a first direction, wherein the projection is located on a closure and wherein the projection is so constructed and arranged so as to be incompatible with any known intravenous spike set;

piercing a membrane of a fluid receptacle with the spike member;

pushing at least two rib members located on an interior of the projection in a direction substantially perpendicular to the first direction tearing the membrane with the spike member wherein the at least two rib members each comprise a face extending substantially parallel to a vertical axis through a center of the projection, the face being exposed for contacting the spike member; and delivering the medical fluid to a patient.

21. The method of claim 20, comprising forming a ventilation hole during the tearing.

22. The method of claim 20, wherein the medical fluid is delivered through the spike member.

23. The method of claim 20, the closure comprising an aperture that extends though a top surface and a bottom surface of the closure.

24. The method of claim 20, the method comprising threading the spike member onto the projection.

25. The method of claim 20, the, method comprising attaching the spike member to a medical tube selected from the group consisting of gastrostomy, percutaneous, jejunostomy, nasogastric and combinations thereof.

* * * * *